United States Patent
Björck et al.

(10) Patent No.: US 9,784,741 B2
(45) Date of Patent: Oct. 10, 2017

(54) DIAGNOSTIC METHOD

(71) Applicant: Hansa Medical AB, Lund (SE)

(72) Inventors: Lars Björck, Lund (SE); Bertil Christensson, Lund (SE); Heiko Herwald, Veberöd (SE); Adam Linder, Lund (SE); Per Åkesson, Lund (SE)

(73) Assignee: Hansa Medical AB, Lund (SE)

( * ) Notice: Subject to any disclaimer, the term of this patent is extended or adjusted under 35 U.S.C. 154(b) by 0 days.

(21) Appl. No.: 14/094,679

(22) Filed: Dec. 2, 2013

(65) Prior Publication Data

US 2014/0187503 A1 Jul. 3, 2014

Related U.S. Application Data

(60) Continuation of application No. 13/797,749, filed on Mar. 12, 2013, now abandoned, which is a division of application No. 12/161,330, filed as application No. PCT/EP2008/004743 on Jun. 12, 2008, now Pat. No. 8,518,648.

(30) Foreign Application Priority Data

Jun. 12, 2007 (GB) .................................. 0711327.7

(51) Int. Cl.
*G01N 33/569* (2006.01)
*G01N 33/68* (2006.01)

(52) U.S. Cl.
CPC ....... *G01N 33/569* (2013.01); *G01N 33/6893* (2013.01); *G01N 2800/26* (2013.01)

(58) Field of Classification Search
CPC ........ G01N 2800/26; A61B 5/41; A61B 5/412
See application file for complete search history.

(56) References Cited

U.S. PATENT DOCUMENTS

| | | | |
|---|---|---|---|
| 5,420,016 | A | 5/1995 | Boguslaski et al. |
| 5,627,262 | A | 5/1997 | Pereira |
| 5,962,241 | A | 10/1999 | Ax et al. |
| 5,976,536 | A | 11/1999 | Stephens et al. |
| 6,303,321 | B1 | 10/2001 | Tracey et al. |
| 7,655,480 | B2 | 2/2010 | Pereira |
| 7,767,395 | B2 | 8/2010 | Garrett et al. |
| 8,518,648 | B2 | 8/2013 | Björck et al. |
| 2003/0170745 | A1 | 9/2003 | Pereira |
| 2004/0197930 | A1 | 10/2004 | Rosenfeld et al. |
| 2005/0196817 | A1 | 9/2005 | Kingsmore et al. |
| 2006/0173162 | A1 | 8/2006 | Djurup et al. |

(Continued)

FOREIGN PATENT DOCUMENTS

| | | |
|---|---|---|
| WO | WO/95/28949 A1 | 11/1995 |
| WO | WO 98/32390 | 7/1998 |

(Continued)

OTHER PUBLICATIONS

Bossink et al., 1999, "The Clinical Host Response to Microbial Infection in Medical Patients with Fever," *Chest* 116(2):380-390.

(Continued)

*Primary Examiner* — Rebecca Martinez
(74) *Attorney, Agent, or Firm* — Dechert LLP

(57) ABSTRACT

It has been demonstrated that the level of HBP increases in individuals that subsequently develop severe sepsis. Accordingly, the level of HBP, HBP/WBC ratio or HBP/NC ratio in an individual can be used to determine whether or not an individual is at risk of developing severe sepsis.

12 Claims, 8 Drawing Sheets

(56) References Cited

U.S. PATENT DOCUMENTS

| | | |
|---|---|---|
| 2007/0092911 A1 | 4/2007 | Buechler et al. |
| 2007/0110804 A1 | 5/2007 | Royer |
| 2007/0166768 A1 | 7/2007 | Pereira |
| 2007/0269437 A1 | 11/2007 | Djurup et al. |
| 2009/0221021 A1 | 9/2009 | Chalumeau et al. |
| 2014/0080754 A1 | 3/2014 | Björck et al. |
| 2014/0080925 A1 | 3/2014 | Björck et al. |

FOREIGN PATENT DOCUMENTS

| | | |
|---|---|---|
| WO | WO/00/47104 A2 | 8/2000 |
| WO | WO/03/076459 A1 | 9/2003 |
| WO | WO 2004/016653 A2 | 2/2004 |
| WO | WO/2004/088324 A2 | 10/2004 |
| WO | WO/2004/112713 A2 | 12/2004 |
| WO | WO/2005/028512 A1 | 3/2005 |
| WO | WO 2007/068830 A1 | 6/2007 |
| WO | WO 2008/151808 A1 | 12/2008 |
| WO | WO 2012/038541 A1 | 3/2012 |
| WO | WO 2012/107450 A1 | 8/2012 |

OTHER PUBLICATIONS

Gautam et al., 2001, "Heparin-Binding Protein (HBP/CAP37): A Missing Link in Neutrophil-Evoked Alteration of Vascular Permeability," *Nat Med.* 7(10):1123-1127.

Lennard, et al., 1982, "Implications of Leukocytosis and Fever at Conclusion of Antibiotic Therapy for Intra-abdominal Sepsis," *Ann of Surgery*, 195(1):19-24.

Linder et al., 2009, "Heparin-Binding Protein: An Early Marker of Circulatory Failure in Sepsis," *Clin Infect Dis.* 49(7):1044-1150.

O'Grady et al., 1999, "Detection of Macrophage Inflammatory protein (MIP)-1α and MIP-1β during Experimental Endotoxemia and Human Sepsis," *J Infect Dis.* 179:136-141.

PCT International Search Report from PCT/EP2008/004743 dated Nov. 11, 2008.

PCT International Preliminary Report on Patentability for PCT/EP2008/004743, dated Nov. 8, 2009.

Reining et al., 2001, *Nat Med.* 7:S87.

Soehnlein et al., 2005, "Neutrophil-Derived Heparin-Binding Protein (HBP/CAP37) Deposited on Endothelium Enhances Monocyte Arrest under Flow Conditions," *J Immunol.* 174:6399-6405.

UK Intellectual Property Office Search Report from GB0711327.7 dated Aug. 22, 2007.

Weiss et al., 2003,"Transient Leukocytosis, Granulocyte Colony-Stimulating Factor Plasma Concentrations, and Apoptosis Determined by Binding of Annexin V by Peripheral Leukocytes in Patients with Severe Sepsis," *Ann N.Y Acad. Sci.* 1010:742-747.

Wolpe et al., 1989, "Macrophage Inflammatory proteins 1 and 2: Members of a Novel Superfamily of Cytokines," *FASEB J.* 3:2565-2573.

Claessens, 2007 "Diagnosis and Treatment of Severe Sepsis," *Critical Care* 11(Suppl 5):1-8.

Bochud et al., 2004 "Antimicrobial therapy for patients with severe sepsis and septic shock: An evidence-based review," *Crit Care Med.* 32(11 Suppl.):S495-S512.

Behling-Kelly et al., (2006) "Roles of cellular activation and sulfated glycans in Haemophilus somnus adherence to bovine brain microvascular endothelial cells," *Infection and Immunity* 74(9):5311-5318.

Beran et al., (2010) "Heparin-binding Protein as a Biomarker of Circulatory Failure during Severe Infections: A Report of Three Cases," *Scandinavian Journal of Infectious Diseases* 42:634-636.

Kahn et al., (2002) "Contact-System Activation in Children with Vasculitis" *National Library of Medicine* Abstract No. 12241658.

Kjölvmark et al., (2012) "Elevated Urine Levels of Heparin-Binding Protein in Children with Urinary Tract Infection," *Pediatr Nephrol* 27(8):1301-1308.

Linder et al., (2010) "Roles of Heparin-Binding Protein in Bacterial Infections," *Journal of Innate Immunity* 2:431-438.

Linder et al., (2011) "Heparin-binding Protein: A Diagnostic Marker of Acute Bacterial Meningitis," *Critical Care Medicine* 39(4):812-817.

Mariscalco et al., (2011) "Heparin-binding Protein: Another Neutrophil Granule Protein . . . Another New Biomarker?," *Critical Care Medicine* 39(4):910-911.

Mussap et al., (2006) "Laboratory Investigation for the Early Diagnosis and Monitoring of Neonatal Urinary Tract Infections: the Present Situation and Future Perspectives," *Journal of Chemotherapy* 18(3):9-13.

Pereira et al., (1989) "Quantitation of a cationic antimicrobial granule protein of human polymorphonuclear leukocytes by ELISA," *J Immunological Methods* 117:115-120.

Peltola et al., (2006) "Comparison of total white blood cell count and serum C-reactive protein levels in confirmed bacterial and viral infections," *J Peds* 149(5):721-724.

Serruto et al., (2010) "Neisseria Meningitidis GNA2132, A Heparin-Binding Protein that Induces Protective Immunity in Human," *Proc. Natl. Acad. Sci USA.* 107(8):3770-3775.

Tapper et al., (2002) "Secretion of Heparin-binding Protein from Human Neutrophils is determined by its Localization in Azurophilic Granules and Secretory Vesicles," *Blood*, 99(5):1785-1793.

UK IPO Search Report from GB1016161.0 dated Apr. 15, 2011.

Wang et al., (2006) "Specific Cleavage of Insulin-like Growth Factor-Binding Protein-1 by a Novel Protease Activity," *Cellular and Molecular Life Sciences* 63(19-20):2405-2414, XP019440764.

Woodford et al., (2011) "Diagnosis and Management of Urinary Infections in Older People," *Clinical Medicine, Royal College of Physicians* 11(1):80-83.

Yoshida et al., (2008) "Expression of the Heparin-Binding Growth Factor Midkine in the Cerebrospinal of Patients with Neurological Disorders," *Internal Medicine* 47(2):83-89.

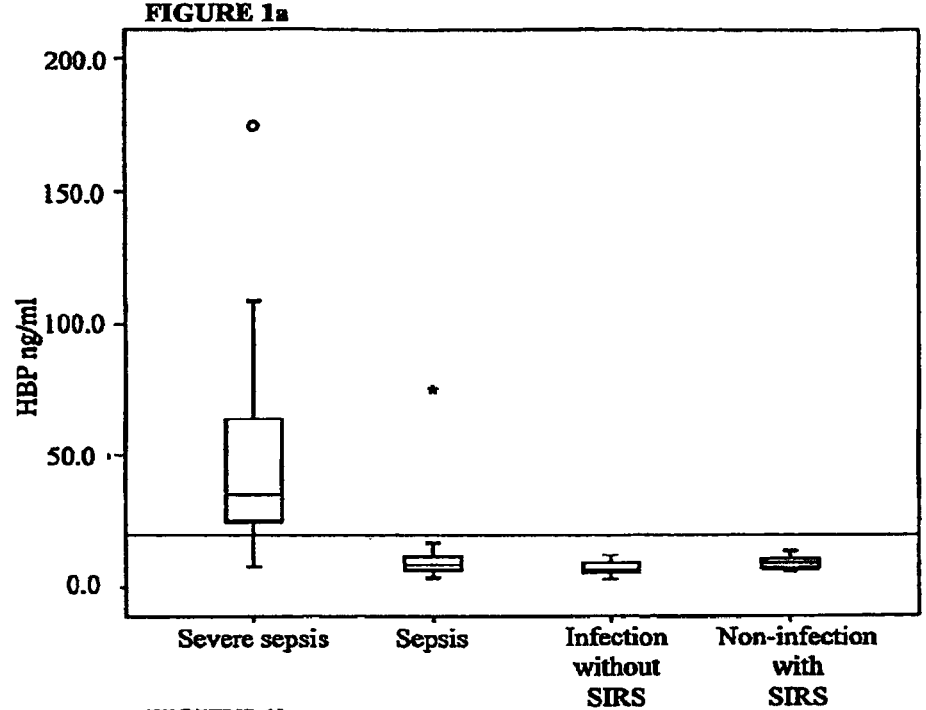
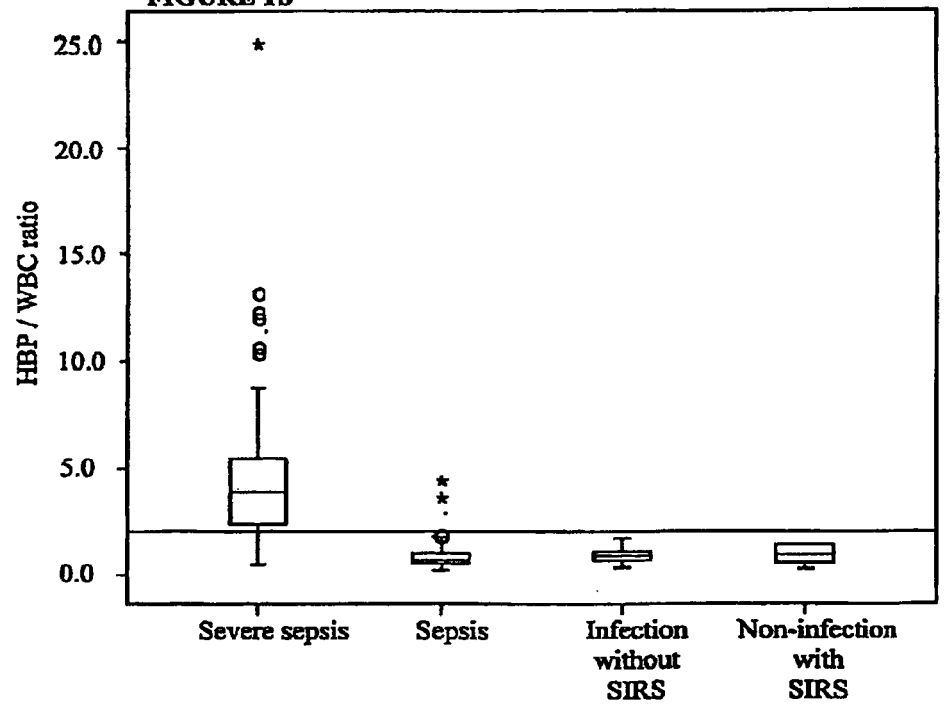

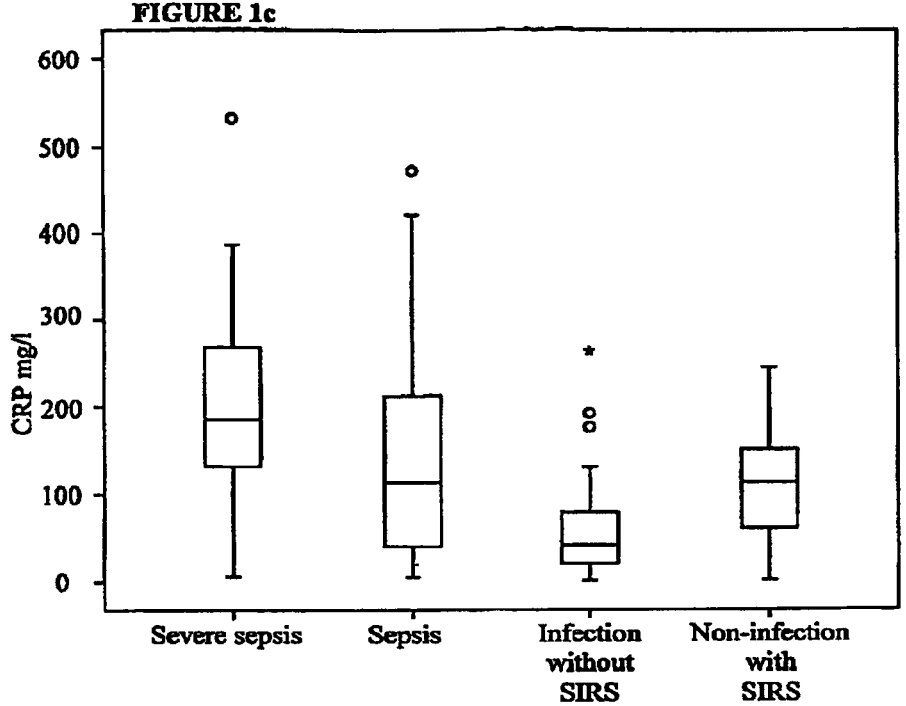
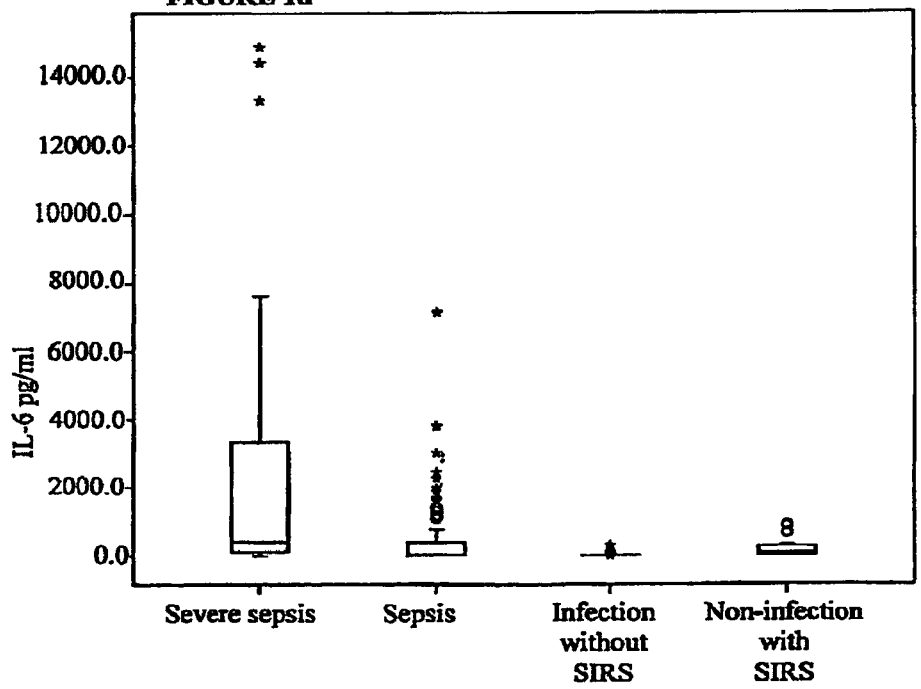

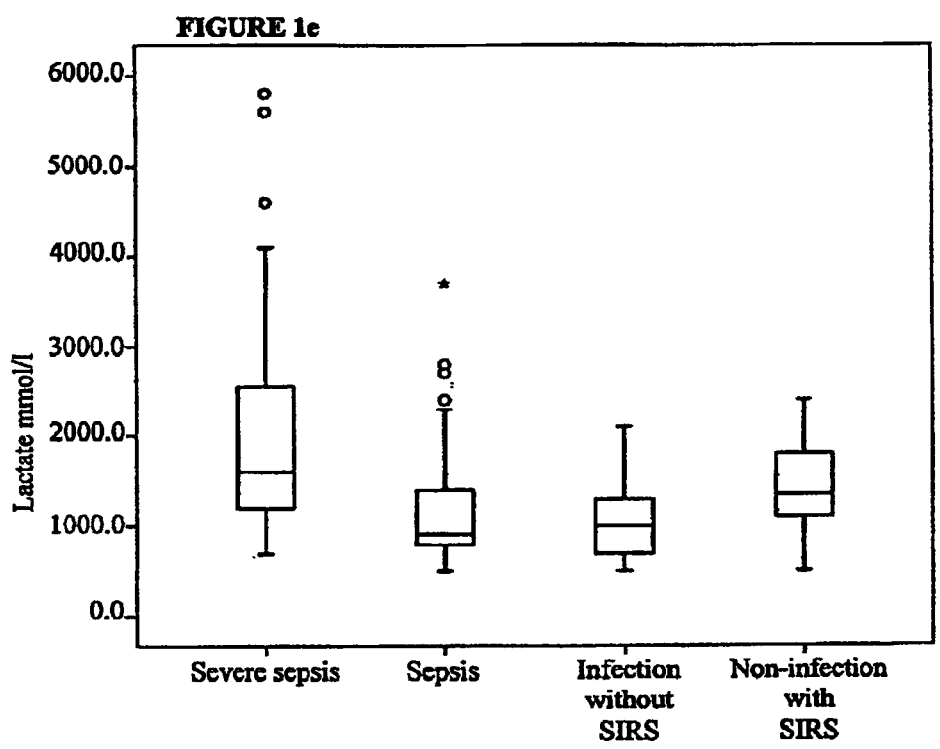

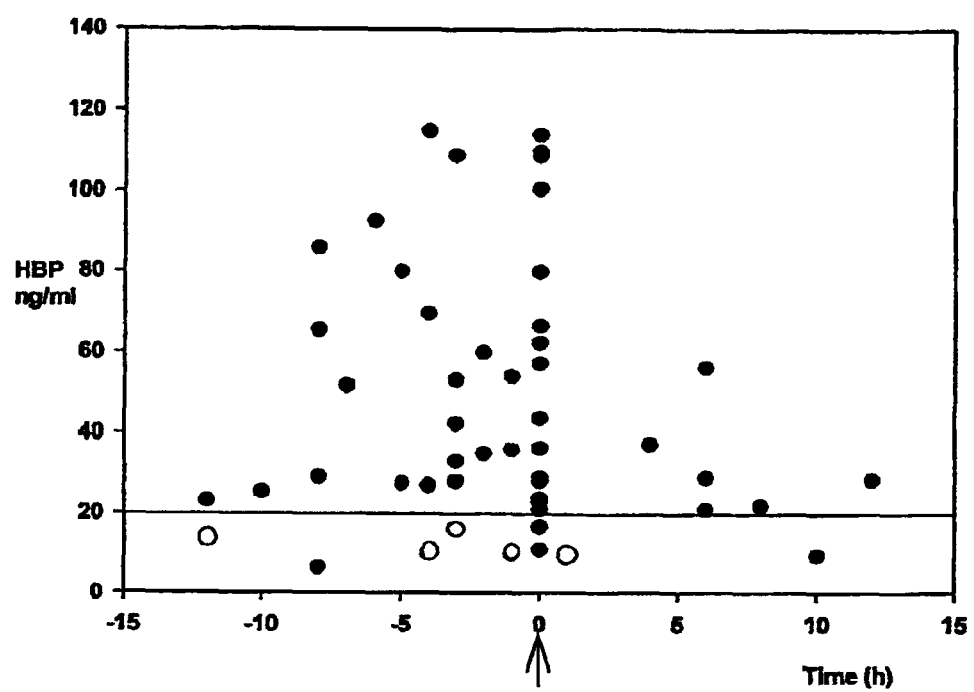

SEQUENCE LISTING

```
<160> NUMBER OF SEQ ID NOS: 1

<210> SEQ ID NO 1
<211> LENGTH: 222
<212> TYPE: PRT
<213> ORGANISM: homo sapiens

<400> SEQUENCE: 1

Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
                20                  25                  30

Ala Arg Phe Val Met Thr Ala Ala Ser Cys Phe Gln Ser Gln Asn Pro
            35                  40                  45

Gly Val Ser Thr Val Val Leu Gly Ala Tyr Asp Leu Arg Arg Arg Glu
        50                  55                  60

Arg Gln Ser Arg Gln Thr Phe Ser Ile Ser Ser Met Ser Glu Asn Gly
65                  70                  75                  80

Tyr Asp Pro Gln Gln Asn Leu Asn Asp Leu Met Leu Leu Gln Leu Asp
                85                  90                  95

Arg Glu Ala Asn Leu Thr Ser Ser Val Thr Ile Leu Pro Leu Pro Leu
            100                 105                 110

Gln Asn Ala Thr Val Glu Ala Gly Thr Arg Cys Gln Val Ala Gly Trp
        115                 120                 125

Gly Ser Gln Arg Ser Gly Gly Arg Leu Ser Arg Phe Pro Arg Phe Val
130                 135                 140

Asn Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
            180                 185                 190

Leu Gly Pro Cys Gly Arg Gly Pro Asp Phe Phe Thr Arg Val Ala Leu
        195                 200                 205

Phe Arg Asp Trp Ile Asp Gly Val Leu Asn Asn Pro Gly Pro
210                 215                 220
```

DIAGNOSTIC METHOD

CROSS REFERENCE TO RELATED APPLICATIONS

This application is a continuation of U.S. patent application Ser. No. 13/797,749, filed on Mar. 12, 2013, which is a divisional of U.S. patent application Ser. No. 12/161,330, filed on Aug. 12, 2010, which is a national stage of International Application No. PCT/EP2008/004743, filed on Jun. 12, 2008, which claims priority under 35 U.S.C. §§119(a)-(d) and 365(b) to United Kingdom Application No. 0711327.7, filed on Jun. 12, 2007, the contents of each of which are incorporated herein in their entireties by reference.

FIELD OF THE INVENTION

The invention relates to the diagnosis of susceptibility to and the prevention of the development of severe sepsis.

BACKGROUND OF THE INVENTION

Sepsis is a systemic inflammatory response to infection, which causes organ failure and death in severe cases. It is an increasingly common cause of morbidity and mortality, particularly in elderly, immuno-compromised, and critically ill individuals. Sepsis has been reported to be the most common cause of death in the non-coronary intensive care unit (Bone R C et al; Chest. 1992 June; 101(6):1644-55). It occurs in 1-2% of all hospitalizations and mortality rates range from 20% for sepsis to 40% for severe sepsis to >60% for septic shock (a sub-category of severe sepsis) (Leibovici; Ann Intern Med 1991; 114(8):703, Martin et al; N Engl J Med. 2003 Apr. 17; 348(16):1546-54).

The clinical definition of sepsis is the presence of two or more of the following conditions:

(1) fever (temperature >38° C.) or hypothermia (temperature <36° C.);
(2) heart rate >90 beats per minute;
(3) respiratory rate >20 breaths per minute or $PaCO_2$<32 mm Hg; and
(4) white blood cell count >12 ($\times 10^9$ cells/L) or <4 ($\times 10^9$ cells/l), at the same time as a confirmed or suspected infection.

Conditions (1) to (4) are known as the SIRS (Severe Inflammatory Response Syndrome) criteria (Bone R C et al; Chest. 1992 June; 101(6):1644-55) and are a recognised international standard for diagnosis of severe inflammation. An individual exhibiting two or more of the SIRS criteria without a confirmed or suspected infection is classified as having non-infection associated SIRS.

The clinical definition of severe sepsis is sepsis as defined above, associated with sepsis-induced hypotension, organ dysfunction or perfusion abnormalities. Sepsis-induced hypotension is defined as a systolic blood pressure of <90 mm Hg or a reduction of <40 mm Hg from baseline in the absence of other causes of hypotension. Perfusion abnormalities may include, but are not limited to hypoperfusion, lactic acidosis, oliguria, or an acute alteration in mental status. Severe sepsis includes as a sub-category the condition of septic shock. This condition is specifically defined by the presence of sepsis-induced hypotension despite adequate fluid resuscitation along with the presence of perfusion abnormalities. Individuals who are receiving inotropic or vasopressor agents may not be hypotensive at the time that perfusion abnormalities are measured.

For the treatment of severe sepsis, diagnosis prior to the onset of the snore severe symptoms (hypotension, organ dysfunction or hypoperfusion) with the institution of adequate treatment is of the utmost importance for a successful outcome (Rivers E at al. N Engl J Med 2001; 345(19): 1368-77). For example, Kumar et al showed that mortality was correlated to the number of hours passed after the onset of sepsis-induced hypotension before the first treatment was given (Kumar et al. Crit Care Med 2006; 34(6):1589-96). A reliable biological or clinical marker to determine as early as possible whether an individual is at risk of developing severe sepsis is needed to minimise the delay before the institution of treatment,

SUMMARY OF THE INVENTION

Heparin-binding protein (HBP, CAP37, Azurocidin) is a glycosylated, single chain, negatively, charged 37 kDa inactive serine protease homologue exhibiting 44% sequence identity with human neutrophil elastase. The three dimensional structure of HBP has been published (Iversen et al Nat Struct Biol. 1997 April; 4(4):265-8). It is contained in the azurofilic granulae of human neutrophils (Lindmark at al, J Leukoc Biol 1999; 66(4):634-43). It is a multifunctional protein that has been shown to induce vascular leakage by altering the $Ca^{2+}$ balance of the blood vessel cytoskeleton (Gautam et al, Nature Medicine 2001; 7(10):1123-7). The M-protein of group A streptococci (GAS) in complex with fibrinogen has been shown to induce HBP release by stimulation of the B2-integrin receptor of neutrophils (Herwald et al, Cell 2004; 116(3):367-79). LPS can also induce HBP release by an unknown mechanism (Rasmussen at al, FEBS Lett 1996; 390(1):109 12). The sequence of HBP is publically available (for example as NCBI accession no. NP_001691 REGION: 27 . . . 248) and is reproduced below as SEQ ID NO.1

```
                                                      SEQ ID NO: 1
IVGGRKARPRQFPFLASIQNQGRHFCGGALIHARFVMTAASCFQSQNPGVSTVVLGAYDLRRRE

RQSRQTFSISSMSENGYDPQQNLNDLMLLQLDREANLTSSVTILPLPLQNATVEAGTRCQVAGW

GSQRSGGRLSRFPRFVNVTVTPEDQCRPNNVCTGVLTRRGGICNGDGGTPLVCEGLAHGVASFS

LGPCGRGPDFFTRVALFRDWIDGVLNNPGP
```

The HBP levels in individuals exhibiting one or more of the SIRS criteria have not previously been investigated. The inventors have shown for the first time that levels of HBP are increased in individuals who subsequently develop severe sepsis. HBP levels are raised up to 12 hours before sepsis-induced hypotension is recorded, but rapidly decrease if therapy is instituted. The inventors have also shown for the first time that the HBP/White Blood Cell count (WBC) ratio is elevated in individuals who subsequently develop severe sepsis.

According to the invention there is thus provided a method of identifying whether or not an individual is at risk of developing severe sepsis, which method comprises measuring HBP in the individual and thereby determining whether or not the individual is at risk of developing severe sepsis.

The method of the invention may further comprise measuring the WBC or neutrophil count (NC) in an individual, calculating the HBP/WBC ratio or HBP/NC ratio respectively, and thereby determining whether or not the individual is at risk of developing severe sepsis.

The method of the invention may thus comprise measuring the HBP in an individual and calculating the HBP/WBC level or HBP/NC ratio in an individual, and thereby determining whether or not the individual is at risk of developing severe sepsis.

The invention further provides:
an agent for the detection of HBP for use in determining whether or not an individual is at risk of developing severe sepsis;
a test kit for use in a method for determining whether or not an individual is at risk of developing severe sepsis, which test kit comprises an agent for the detection of HBP in an individual;
a method of reducing the risk of an individual developing severe sepsis comprising:
  (i) determining whether or not an individual is at risk of developing severe sepsis using a method of the invention; and
  (ii) administering to an individual identified in (i) as at risk, a therapeutically effective amount of an agent suitable for the treatment of infection and/or intravenous fluids.

DESCRIPTION OF THE FIGURES

FIG. 1 shows HBP concentration (FIG. 1a), HBP/WBC ratios (FIG. 1b), CRP levels (FIG. 1c), IL-6 levels (FIG. 1d) and lactate levels (FIG. 1e) in the severe sepsis group (n=51), sepsis group (n=95), infection without SIRS group (n=44) and SIRS without infection group (n=12). Line within box: median; edges of box: quartiles (Q1, Q3); whiskers: range of values; x and o: outlier values identified by patient number. Lines representing cut-off values for HBP level of 20 ng/ml and HBP/WBC ratio of 2 for FIGS. 1a and 1b respectively

DETAILED DESCRIPTION OF THE INVENTION

Diagnosis

Figure 2:
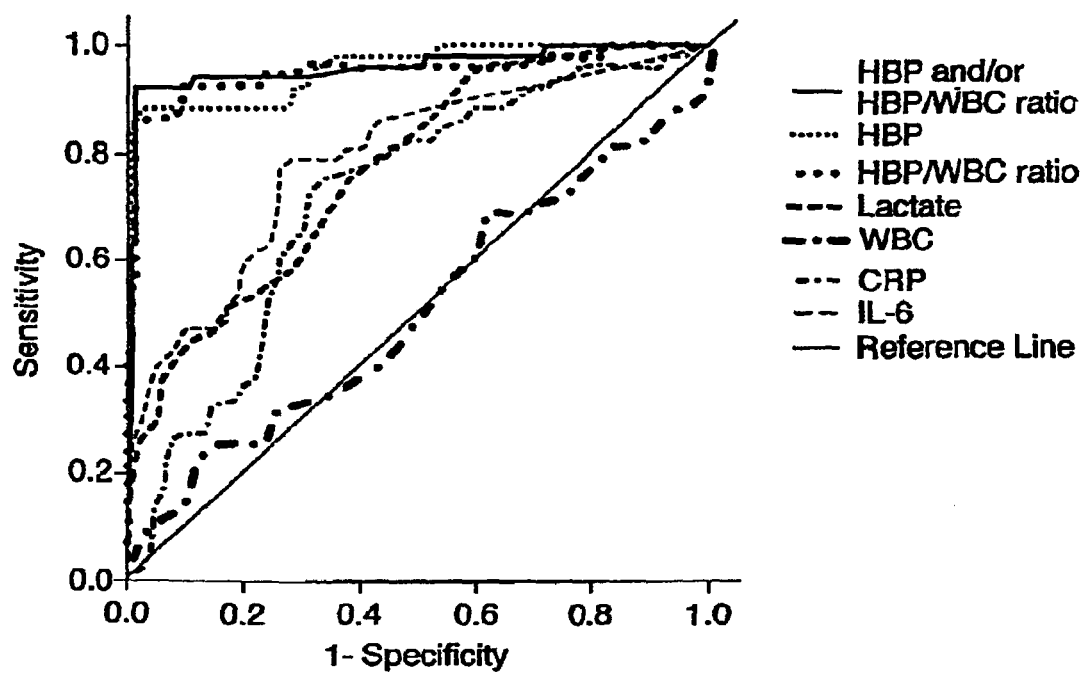
FIG. 2 shows an ROC curve for HBP level and/or HBP/WBC ratio, HBP level, HBP/WBC ratio, lactate, White blood cell count, CRP, and IL-6. The straight line from 0, 0 to 1, 1 is a reference line. Diagonal segments are produced by ties.

The present invention relates to a method of identifying whether or not a subject is at risk of developing severe sepsis. The invention therefore relates to the diagnosis of susceptibility of an individual to severe sepsis. The individual under test is typically suspected of being at risk of developing severe sepsis. The individual is typically a mammal The mammal is typically a human or a domestic mammal such as a horse, a cow, a sheep, a dog or a cat. The individual is preferably a human.

The individual may be suspected of being at risk of developing severe sepsis because they have a confirmed or suspected infection, and/or display one or more, or two or more, of the SIRS criteria. The SIRS criteria are:
(1) fever (temperature >38° C.) or hypothermia (temperature <36° C.);
(2) heart rate >90 beats per minute;
(3) respiratory rate >20 breaths per minute or $PaCO_2$<32 mm Hg; and
(4) white blood cell count >12 ($\times 10^9$ cells/L) or <4 ($\times 10^9$ cells/L).

The confirmed or suspected infection is typically one or more of a bacterial, a parasitic or a fungal infection. A bacterial infection may be caused by one or more Gram negative or Gram positive bacteria. The one or more Gram negative bacteria may be selected from *Escherichia coli*, *Klebsiella* spp. (typically *K. pneumoniae* or *K.oxytoca*), *Enterobacter* spp (typically *E. cloacae* or *E. aerogenes*), *Bordetella* spp. (typically *B. bronchiseptica*, *B. pertussis* or *B. parapertussis*), *Chlamydia* spp. (typically *C. trachomatis*), *Legionella* spp. (typically *L. pneumophilia*), *Pseudomonas* spp. (typically *P. aeruginosa*), *Mycoplasma* spp. (typically *M. pneumoniae*), *Haemophilus influenza*, *Serratia marcescens*, *Proteus mirabilis*, *Acinetobacter baumannii*, *Stenotrophomonas maltophilia* and *Neisseria meningitidis* (typically of serogroup A, B, C, H, I, K, L, X, Y, Z, 29E or W135). The one or more Gram positive bacteria may be selected from *Staphylococcus* spp. (typically *S. aureus* or Coagulase negative *Staphylococci*), *Streptococcus* spp. (typically *S. pneumoniae* or *S. pyogenes*) and *Enterococcus* spp. (typically *E. faecium* or *E. faecalis*). A fungal infection may be caused by one or more fungi selected from *Candida albicans*, *Candida tropicalis*, *Candida parapsilosis*, *Candida krusei*, *Candida glabrata* and *Aperigillus fumigatus*.

The confirmed or suspected infection may affect any part of the body. Typical examples include an infection which affects the lungs; the respiratory tract; the liver; the kidneys; the urinary tract; the skin (cutaneous and subcutaneous); the heart; the stomach; the intestines; the blood; the tales; the joints or any combination thereof. The confirmed or suspected infection may be meningitis.

The infection may be confirmed by diagnostic practices known in the art, for example microbial culture of samples taken from the individual, antigen testing of urine or other fluid samples taken from the individual (especially for *S. pneumoniae* and *Legionella* sp. infections) or PCR analysis (especially for atypical pneumonia caused by bacterial infection e.g. *Mycoplasma*, *Legionella*, *Chlamydia*, and *B. pertussis*). More recently multiplex PCR techniques have been developed which enable simultaneous testing for multiple bacterial and fungal infections.

The infection may be suspected because Of the presence of one or more of the following general symptoms: fever higher than 38° C.; chills; pain; an ache or tenderness; general feeling of tiredness; night sweats; and a wound or incision with associated redness, heat, swelling or pain, or that exudes a fluid that is white, yellowish or greenish.

The present invention may be used to confirm susceptibility in an individual with one or more additional risk factors and/or one or more predispositions toward the development of severe sepsis. Risk factors that increase susceptibility to developing severe sepsis typically include any factor which increases susceptibility to infection. These factors can include a weakened immune system (i.e. the individual is immuno-compromised), or the presence in a hospitalised patient of an intravenous line, surgical wound, surgical drain, or a site of skin breakdown known as decubitus ulcers or bedsores. A diabetic individual is more prone to developing severe sepsis. The diagnostic method of the invention may be carried out in conjunction with another assay or genetic test to refine risk prediction.

Typically, the individual does not have a chronic inflammatory-associated disease and/or displays no symptoms which are specifically associated with such diseases. Examples of such diseases include atherosclerosis, Alzheimer's disease, asthma, rheumatoid arthritis, osteoarthritis, and inflammatory diseases of the bowel such as Crohn's disease, Ulcerative colitis, Irritable bowel syndrome and Inflammatory bowel disease. If the individual does have a chronic inflammatory-associated disease, they additionally have a confirmed or suspected infection as defined above, and/or display one or more, or two or more, of the SIRS criteria.

Typically, the individual does not have severe sepsis or displays no symptoms which would lead to a diagnosis of severe sepsis. Typically such symptoms include sepsis-induced hypotension, organ dysfunction or perfusion abnormalities. Sepsis-induced hypotension is defined as a systolic blood pressure of <90 mm Hg or a reduction of <40 mm Hg from baseline in the absence of other causes of hypotension. Perfusion abnormalities may include, but are not limited to hypoperfusion, lactic acidosis, oliguria, or an acute alteration in mental status. Severe sepsis includes as a sub-category the condition of septic shock. This condition is specifically defined by the presence of sepsis-induced hypotension despite adequate fluid resuscitation along with the presence of perfusion abnormalities. Individuals who are receiving inotropic or vasopressor agents may not be hypotensive at the time that perfusion abnormalities are measured.

The present invention involves measuring the level of HBP in an individual. Typically the level of HBP is measured by determining the concentration of HBP in a fluid sample taken from the individual. According to the present invention, an increased level of HBP compared with the baseline level or concentration indicates that the individual is susceptible to or at risk of developing severe sepsis. The baseline level is typically the level of HBP in an individual who is suspected of being at risk of developing severe sepsis but does not subsequently develop severe sepsis. For example the inventors have shown that, when the level of HBP is measured by determining the concentration of HBP in a plasma sample taken from an individual, individuals who develop non-severe sepsis have a median HBP concentration of about 8.5 ng/ml, individuals who have a confirmed or suspected infection but display one or fewer SIRS criteria have a median HBP concentration of about 6.5 ng/ml, and individuals who display of two or more SIRS criteria in the absence of infection have a median HBP concentration of about 9 ng/ml. The median HBP concentration for all categories of individual who are suspected of being at risk of developing severe sepsis but do not subsequently develop severe sepsis is about 8 ng/ml.

In the present invention, in a fluid sample taken from an individual an increased concentration of HBP associated with increased susceptibility to or risk of developing severe sepsis is typically greater than about 15 ng/ml, or greater than about 16, 17, 18, 19, 20, 21, 22, 23 or 24 ng/ml. The increased concentration of HBP associated with increased susceptibility to or risk of developing severe sepsis is preferably greater than about 20 ng/ml.

According to the present invention, the increase in HBP level or concentration associated with increased susceptibility to or risk of developing severe sepsis is at least 2 fold, 2.5 fold or 3 fold relative to the baseline level or concentration. The increase in HBP level or concentration associated with increased susceptibility to or risk of developing severe sepsis is preferably at least 2.5 fold relative to the baseline level or concentration.

The present invention may therefore also involve assessment of the ratio of HBP/white blood cell count (WBC) to determine the risk of developing severe sepsis.

According to the present invention, an increased HBP/WBC ratio compared with the baseline ratio indicates that the individual is susceptible to or at risk of developing severe sepsis. The baseline ratio is typically the HBP/WBC ratio in an individual who is suspected of being at risk of developing severe sepsis but does not subsequently develop severe sepsis. When the concentration of HBP in a fluid sample is measured in ng/ml and the WBC in a blood sample is measured in number of cells×$10^9$/l, the inventors have shown that, for example, individuals who develop non-severe sepsis have a median HBP/WBC ratio of about 0.7:1, individuals who have a confirmed or suspected infection but display one or fewer SIRS criteria have a median HBP/WBC ratio of about 0.85:1, and individuals who display of two or more SIRS criteria in the absence of infection have a median HBP/WBC ratio of about 0.9:1. The median HBP/WBC ratio for all categories of individual who are suspected of being at risk of developing severe sepsis but do not subsequently develop severe sepsis is about 0.75:1.

In the present invention, when the concentration of HEW in a fluid sample is measured in ng/ml and the WBC count in a blood sample is measured in number of cells×$10^9$/l, an increased HBP/WBC ratio associated with increased susceptibility to or risk of developing severe sepsis is typically greater than about 1.4:1, or greater than about 1.5:1, 1.6:1, 1.7:1, 1.8:1, 1.9:1, 2.0:1, 2.1:1, 2.2:1, 23:1 or 2.4:1. The increased HBP/WBC ratio associated with increased susceptibility to or risk of developing severe sepsis is preferably greater than about 2.0:1.

According to the present invention, the increase in HBP/WBC ratio associated with increased susceptibility to or risk of developing severe sepsis is at least 1.5 fold, 2 fold, 2.5 fold or 3 fold relative to the baseline ratio. The increase in HBP/WBC ratio associated with increased susceptibility to or risk of developing severe sepsis is preferably at least 2.5 fold relative to the baseline ratio.

The present inventors have determined the mean neutrophil count (NC) in individuals suspected of being at risk of developing severe sepsis is about 80% of the white blood cell count (WBC). The present invention may also assess the ratio of HBP/NC to determine the risk of developing severe sepsis.

According to the present invention, an increased HBP/NC ratio compared with the baseline ratio indicates that an individual is susceptible to or at risk of developing severe sepsis. The baseline ratio is typically the HBP/NC ratio in an individual who does not have an infection and/or does not display any of the SIRS criteria. When the concentration of HBP in a fluid sample is measured in ng/ml and the NC count in a blood sample is measured in number of cells×$10^9$/l, the inventors have shown that, for example, individuals who develop non-severe sepsis have a median HBP/NC ratio of about 0.55:1, individuals who have a confirmed or suspected infection but display one or fewer SIRS criteria have a median HBP/NC ratio of about 0.65:1, and individuals who display of two or more SIRS criteria in the absence of infection have a median HBP/NC ratio of about 0.7:1. The median HBP/NC ratio for all categories of individual who are suspected of being at risk of developing severe sepsis but do not subsequently develop severe sepsis is about 0.6:1.

In the present invention, when the concentration of HBP in a fluid sample is measured in ng/ml and the NC count in a blood sample is measured in number of cells×$10^9$/l, an increased HBP/NC ratio associated with increased susceptibility to or risk of developing severe sepsis is typically greater than about 1.1:1, or greater than about 1.2:1, 1.3:1, 1.4:1, 1.5:1, 1.6:1, 1.7:1, 1.8:1 or 1.9:1. The increased HBP/NC ratio associated with increased susceptibility to or risk of developing severe sepsis is preferably greater than about 1.6:1.

According to the present invention, the increase in HBP/NC ratio associated with increased susceptibility to or risk of developing severe sepsis is at least 1.5 fold, 2 fold, 2.5 fold or 3 fold relative to the baseline ratio. The increase in HBP/NC ratio associated with increased susceptibility to or risk of developing severe sepsis is preferably at least 2.5 fold relative to the baseline ratio.

The invention is typically carried out in vitro on a sample obtained from the individual. The sample typically comprises a body fluid of the individual. The sample is preferably a blood, plasma, serum, urine, cerebrospinal fluid or joint fluid sample. The sample is most preferably a blood sample. The sample is typically processed prior to being assayed, for example by centrifugation. The sample may also be typically stored prior to assay, preferably below −70° C.

Standard methods known in the art may be used to assay the level of HBP. These methods typically involve using an agent for the detection of HBP. The agent typically binds specifically to HBP. The agent may be an antibody specific for HBP. By specific, it will be understood that the agent or antibody binds to HBP with no significant cross-reactivity to any other molecule, particularly any other protein. For example, an agent or antibody specific for IMP will show no significant cross-reactivity with human neutrophil elastase. Cross-reactivity may be assessed by any suitable method.

An antibody used in the method of the invention may either be a whole antibody or a fragment thereof which is capable of binding to HBP. The antibody may be monoclonal. Such a whole antibody is typically an antibody which is produced by any suitable method known in the art. For example, polyclonal antibodies may be obtained by immunising a mammal, typically a rabbit or a mouse, with HBP under suitable conditions and isolating antibody molecules from, for hybridoma or recombinant methods.

Hybridoma methods involve immunising a mammal, typically a rabbit or a mouse, with HBP under suitable conditions, then harvesting the spleen cells of said mammal and fusing them with Myeloma cells. The mixture of fused cells is then diluted and clones are grown from single parent cells. The antibodies secreted by the different clones are then tested for their ability to bind to HBP, and the most productive and stable clone is then grown in culture medium to a high volume. The secreted antibody is collected and purified.

Recombinant methods involve the cloning into phage or yeast of different immunoglobulin gene segments to create libraries of antibodies with slightly different amino acid sequences. Those sequences which give rise to antibodies which bind to HBP may be selected and the sequences cloned into, for example, a bacterial cell line, for production.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody. The antibody can be any class or isotype of antibody, for example IgM, but is preferably IgG.

The fragment of whole antibody that can be used in the method comprises an antigen binding site, e.g. Fab or F(ab)2 fragments. The whole antibody or fragment may be associated with other moieties, such as linkers which may be used to join together 2 or more fragments or antibodies. Such linkers may be chemical linkers or can be present in the form of a fusion protein with the fragment or whole antibody. The linkers may thus be used to join together whole antibodies or fragments which have the same or different binding specificities, e.g. that can bind the same or different polymorphisms. The antibody may be a bispecific antibody which is able to bind to two different antigens, typically any two of the polymorphisms mentioned herein. The antibody may be a 'diabody' formed by joining two variable domains back to back. In the case where the antibodies used in the method are present in any of the above forms which have different antigen binding sites of different specificities then these different specificities are typically to polymorphisms at different positions or on different proteins. In one embodiment the antibody is a chimeric antibody comprising sequence from different natural antibodies, for example a humanised antibody.

Methods to assess HBP level typically involve contacting a sample with an agent or antibody capable of binding specifically to HBP. Such methods may include dipstick assays and Enzyme-linked Immunosorbant Assay (ELISA). Typically dipsticks comprise one or more antibodies or proteins that specifically bind HBP. If more than one antibody is present, the antibodies preferably have different non-overlapping determinants such that they may bind to HBP simultaneously.

ELISA is a heterogeneous, solid phase assay that requires the separation of reagents. ELISA is typically carried out using the sandwich technique or the competitive technique. The sandwich technique requires two antibodies. The first specifically binds HBP and is bound to a solid support. The second antibody is bound to a marker, typically an enzyme conjugate. A substrate for the enzyme is used to quantify the HBP-antibody complex and hence the amount of HBP in a sample. The antigen competitive inhibition assay also typically requires an HBP-specific antibody bound to a support. An HBP-enzyme conjugate is added to the sample (containing HBP) to be assayed. Competitive inhibition between the HBP-enzyme conjugate and unlabeled HBP allows quantification of the amount of HBP in a sample. The solid supports for ELISA reactions preferably contain wells.

The present invention may also employ methods of measuring HBP that do not comprise antibodies. High Performance Liquid Chromatography (HPLC) separation and fluorescence detection is preferably used as a method of determining the HBP level. HPLC apparatus and methods as described previously may be used (Tsikas D et al. J Chromatogr B Biomed Sci Appl 1998; 705: 174-6) Separation during HPLC is typically carried out on the basis of size or charge. Prior to HPLC, endogenous amino acids and an internal standard L-homoarginine are typically added to assay samples and these are phase extracted on CBA cartridges (Varian, Harbor City, Calif.). Amino acids within the samples are preferably derivatized with o-phthalaldehyde (OPA). The accuracy and precision of the assay is preferably determined within quality control samples for all amino acids.

Standard methods known in the art may be used to measure the white blood cell count or neutrophil count in an individual. Such methods included automated or manual counting.

The invention further provides a diagnostic kit that comprises means for measuring the HBP level in an individual and thereby determining whether or not the individual is at risk of developing severe sepsis. The kit typically contains one or more antibodies that specifically bind HBP. For example, the kit may comprise a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')$_2$ or Fv fragment. If more than one antibody is present, the antibodies preferably have different non-overlapping determinants such that they may bind to IMP simultaneously.

The kit may additionally comprise means for the measurement of the WBC count in an individual.

The kit may additionally comprise one or more other reagents or instruments which enable any of the embodiments of the method mentioned above to be carried out. Such reagents or instruments include one or more of the following: suitable buffer(s) (aqueous solutions), means to isolate HBP from sample, means to obtain a sample from the individual (such as a vessel or an instrument comprising a needle) or a support comprising wells on which quantitative reactions can be done. The kit may, optionally, comprise instructions to enable the kit to be used in the method of the invention or details regarding which individuals the method may be carried out upon.

Therapy

The present invention also relates to the treatment of an individual identified by a method of the invention as at risk of developing severe sepsis. Thus, a substance for use in reducing the risk of developing severe sepsis may be used in the manufacture of a medicament for use in the treatment of an individual identified by a method of the invention as at risk of developing severe sepsis. The condition of an individual identified by a method of the invention as at risk of developing severe sepsis can therefore be improved by administration of such a substance. Severe sepsis can thus be prevented. A therapeutically effective amount of a substance useful for reducing the risk of developing severe sepsis may be given to an individual identified by a method of the invention as in need thereof. Substances suitable for reducing the risk of developing severe sepsis typically include one or more antibiotics and/or one or more intravenous fluids. The one or more antibiotics are typically broad spectrum antibiotics. The broad spectrum antibiotics are typically selected from one or more aminoglycosides, cephalosporins, fluoroquinolones, lincosamides, macrolides, penicillins, sulfonamides, or tetracyclines. For example, suitable antibiotics include, but are not limited to, Gentamicin, Kanamycin, Neomycin, Streptomycin, Tobramycin, Cefazolin, Cephalexin, Cephapirin, Cephradine, Cefuroxime, Cefixime, Cefotaxime, Ceftazidime, Ceftizoxime, Ceftriaxone, Ciprofloxacin, Levofloxacin, Ofloxacin, Clindamycin, Azithromycin, Clarithromycin, Erythromycin, Amoxicillin, Ampicillin, Ampicillin-Sulbactam, Cloxacillin, Dicloxacillin, Mezlocillin, Nafcillin, Oxacillin, Penicillin G Benzathine, Penicillin G Potassium, Penicillin G Procaine, Penicillin V Potassium, Piperacillin, Ticarcillin, Ticarcillin-Clavulanate potassium, Pyrimethamine-Sulfadoxine, Sulfadizine, Sulfisoxazole, Sulfmethoxazole, Trimethoprim-sulfamethoxazole, Chlortetracycline, Doxycycline, and Tetracycline.

A substance useful for reducing the risk of developing severe sepsis according to the invention is typically formulated for administration in the present invention with a pharmaceutically acceptable carrier or diluent. The pharmaceutical carrier or diluent may be, for example, an isotonic solution. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of a substance used in the prevention of severe sepsis is administered to a patient identified according to a method of the invention. The dose, for example of an antibiotic, may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific antibiotic, the age, weight and conditions of the subject to be treated and the frequency and route of administration. Preferably, daily dosage levels are from 5 mg to 2 g. That dose may be provided as a single dose or may be provided as multiple doses, for example taken at regular intervals, for example 2, 3 or 4 doses administered daily.

The following Example illustrates the invention:

EXAMPLE

1. Methods

Study Participants 202 adult patients with clinically suspected infection were enrolled in a prospective study at the Infectious Disease Clinic, Lund University Hospital, Sweden, between March 2006 and April 2007. Inclusion criteria were fever >38° C. and antibiotic treatment for less than 24 hours. Duration of antibiotic treatment, demographics, SIRS criteria and systolic blood pressure (SBP) were recorded at admittance. C-reactive protein (CRP), lactate and WBC count were analysed, and plasma samples for later analysis of HBP, IL-6 levels were obtained within 12 hours from admission. In 20 patients serial plasma samples were obtained for up to 96 hours in parallel with recording SIRS criteria and SBP. After discharge, the final diagnosis and 28 d mortality was recorded and the patients were classified according to the SIRS criteria (Bone et al, Chest 1992; 101(6): 1644-55).

Severe sepsis (group 1) was defined as the presence of sepsis and SBP<90 mmHg or a >40 mmHg SBP fall from baseline within 24 h of collection of the blood samples, sepsis (group 2) was defined as display of two or more SIRS criteria together with an infection, non-sepsis (group 3) was defined as display of one SIRS criterion together with an infection, and non-infection (group 4) was defined as display of two or more SIRS criteria together with a non-infectious final diagnosis.

Final infection diagnoses were pneumonia (n=61), upper respiratory tract infection (n=35), urinary tract infection (n=38), cutaneous and subcutaneous infection (n=29), endocarditis (n=4), gastroenteritis (n=12), or other infections including tropical infections (n=11). In 35 patients (17%) bacteremia was diagnosed (17 Gram-negative and 18 Gram-positive bacteria). Non-infectious diagnoses with display of two or more SIRS criteria were pulmonary embolis and systemic vasculitis). Blood samples were collected in 4 mL plastic plasma citrate tubes, immediately centrifuged at 3000 rpm for 10 min, alloquated and stored at −70° C. until analysis.

Analysis of HBP, IL-6, CRP, Lactate, WBC and HBP/WBC Ratio

The concentration of HBP (ng/ml) was determined by a sandwich ELISA as described in (Tapper et al; Blood 2002; 99(5): 1785-93). Plasma samples were diluted 1/40 in PBS and run in duplicates. Recombinant human HBP was produced and purified as described in (Rasmussen et al; FEBS Lett 1996; 390(1):109-12). Mouse monoclonal antibodies (2F23A) and rabbit antiserum (409A) to recombinant HBP were prepared and purified as described in (Lindmark et al; J. Leukoc. Biol 1999; 66(4):634-43) and used at 1/3000 and 1/7000 respectively. Peroxidase-conjugated goat antirabbit IgG from Bio-Rad Laboratories (Richmond, Calif.), were used at 1/3000. A HBP/WBC ratio was calculated by dividing the HBP concentration (ng/ml) with the WBC ($\times 10^9$ cells/L).

IL-6 was measured with a commercial human IL-6 kit (Quantikine, R&D Systems, UK), detection limit 3pg/mL. Plasma samples were diluted 1/40. CRP and lactate analyses were performed on a Roche Hitachi Modular-P with reagents from Roche Diagnostics (Mannheim, Germany) according to the manufacturer's description with the exception that the samples for the lactate analysis were taken from plasma citrate tubes instead of oxalate-fluoride tubes.

White blood cell count (WBC) was measured in a Sysmex XE2100 according to the manufacturer's description (Sysmex).

Statistical analysis

Data are presented as medians, interquartile ranges. Significance testing was carried out using the Mann-Whitney rank sum test. A two-tailed p-value <0.05 was considered statistically significant. Receiver-operating characteristic (ROC) curves (DeLong et al; Biometrics 1988; 44(3): 837-45) and the area under the curve (AUC) were determined for HBP, HBP/WBC ratio, CRP, WBC and IL-6. AUC values are reported with the 95% confidence interval (95% CI). Sensitivities, specificities. positive predictive values and negative predictive values were calculated from cross-tabulations. The positive likelihood ratio and negative likelihood ratio are also reported in Table 1.

2. Results

Characteristics of the Study Participants 202 patients who met the inclusion criteria were included. The patients were classified into the 4 following groups: 51 patients with severe sepsis (group 1), 95 patients with sepsis (group 2), 44 patients with non-sepsis (group 3) and 12 patients with non-infection (group 4), Median age and male/female ratio of the 4 groups were 62 y; 31/20, 57 y; 42/53, 44 r, 15/29, and 73 y; 11/1 respectively. Bacteremia was found in 22, 11, and 2 patients in group 1, 2, and 3 respectively.

Analysis of HBP Levels and HBP/WBC Ratios in Study Participants

At admission, HBP levels were significantly higher in the severe sepsis group (p<0.0001) (FIG. 1a), with 42/51 patients exceeding a cut-off level of 20 ng/ml, as compared to 1/95, 0/44 and 0/12 patients in group 2, group 3 and group 4, respectively. Also, patients in the severe sepsis group showed significantly (p<0.0001) higher HBP/WBC ratios as compared to the other groups (FIG. 1b). A HBP/WBC ratio above 2.0 was found in 44/51 patients in the severe sepsis group, 2/95 patients in the sepsis group, 0/44 patients in the non-sepsis group and 0/12 patients in the non-infection group. Moreover, in the severe sepsis group 47/51 patients had either a plasma HBP level >20 ng/mi or a HBP/WBC ratio >2.0, as compared to 2/95 patients in the sepsis group and 0 patients in the 2 other groups (Table 1).

Similarly, CRP, IL-6 and lactate levels were also significantly higher (p=0.003, p<0.0001, p<0.0001) in the severe sepsis group although there was a considerable overlapping between groups (FIG. 1c-e).

Analysis of Predictive Value of HBP Level and HBP/WBC Ratio

Assuming a 25% prevalence of severe sepsis, as in the present study, the following variables showed better specificity, sensitivity, positive predictive value (PPV), negative predictive value (NPV), positive likelihood ratio (PLR) and negative likelihood ratio (NLR) in diagnosing severe sepsis as compared to all different cut off levels of CRP and IL-6 calculated:

ratory distress and was immediately transferred to the ICU, where ARDS (Adult Respiratory Distress Syndrome) with disseminated intravascular coagulation due to *E. coli* septicemia was later diagnosed. At admission her HBP level was 80 ng/ml and HBP/WBC ratio was 4.2.

TABLE 1a

Sensitivity, specificity, positive predictive value, negative predictive value, positive likelihood ratio and negative likelihood ratio of tested variables in diagnosing severe bacterial sepsis

| Variable | Cut-off | Sensitivity % | Specificity % | PPV % | NPV % | PLR | NLR |
|---|---|---|---|---|---|---|---|
| HBP (ng/ml) | >20 | 82.4 | 99.3 | 97.7 | 94.3 | 118 | 0.18 |
| HBP/WBC ratio | >2 | 86.3 | 98.7 | 95.6 | 95.5 | 66.4 | 0.14 |
| HBP/WBC ratio or HBP level (ng/ml) | >2 or >20 | 92.2 | 98.7 | 95.9 | 97.4 | 71 | 0.08 |
| CRP (mg/l) | >50 | 88.2 | 36.4 | 31.9 | 90.2 | 1.39 | 0.32 |
|  | >100 | 82.3 | 53.6 | 37.5 | 90.0 | 1.77 | 0.33 |
|  | >150 | 64.7 | 71.3 | 42.9 | 85.6 | 2.25 | 0.49 |
|  | >200 | 37.2 | 80.8 | 39.6 | 79.2 | 1.94 | 0.77 |
| IL6 (pg/ml) | >100 | 78.4 | 72.8 | 49.4 | 91.0 | 2.88 | 0.30 |
|  | >200 | 62.7 | 77.5 | 48.5 | 86.0 | 2.78 | 0.48 |
|  | >500 | 47.0 | 84.0 | 50.0 | 82.5 | 2.94 | 0.63 |
|  | >1000 | 43.0 | 90.0 | 59.5 | 82.4 | 4.30 | 0.23 |
| Lactate (mmol/l) | >2.5 | 27.5 | 98.0 | 82.4 | 79.6 | 13.7 | 0.74 |
|  | >2.0 | 41.2 | 91.8 | 63.6 | 81.8 | 5.0 | 0.64 |
|  | >1.5 | 52.9 | 77.6 | 45.0 | 82.6 | 2.4 | 0.61 |
|  | >1 | 88.2 | 46.3 | 36.3 | 91.9 | 1.6 | 0.25 | a HBP level >20 ng/ml indicates individual will develop severe sepsis; or a HBP/WBC ratio >2.0 indicates individual will develop severe sepsis; or either a HBP level >20 ng/ml or a HBP/WBC ratio >2.0 indicates individual will develop severe sepsis These findings are summarised in Tables 1a, 1b and 1c, and are supported by the ROC curve (FIG. 2). Statistical analysis of the ROC curve is shown in table 2.

Figure 3A:
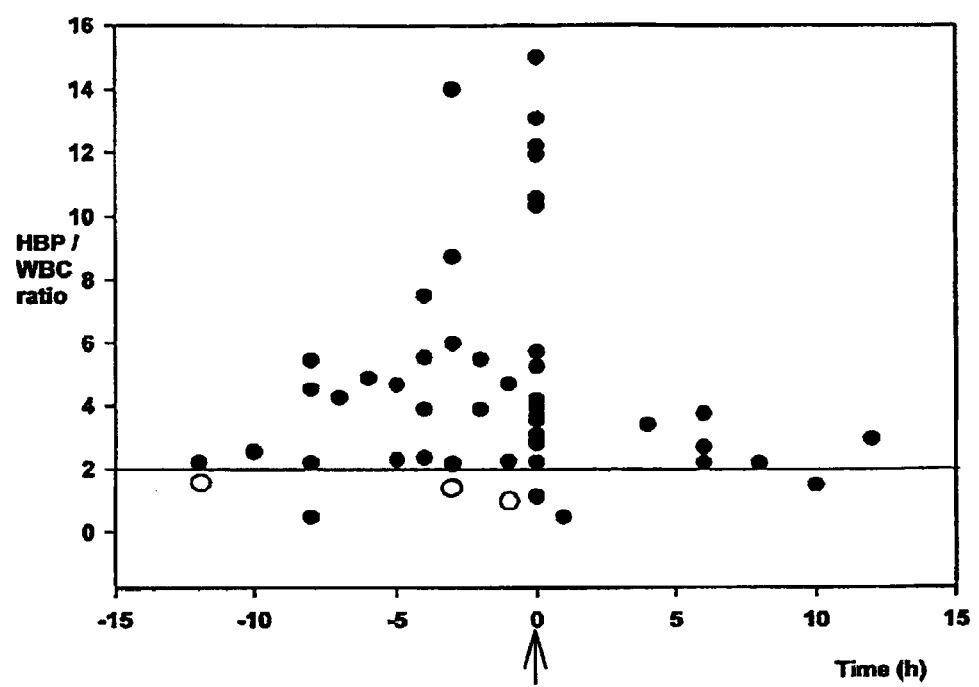
FIG. 3 shows the HBP/WBC ratio (FIG. 3a) or the HBP concentration (FIG. 3b) for each individual (n=51) in the severe sepsis group, plotted against the time from collection of the first plasma sample relative to the time of the lowest measured blood pressure (indicated by the arrow at 0 hrs). Open circles in FIG. 3a represent patients who fell below the HBP/WBC ratio cut off level but scored above the HBP concentration cut off level. Open circles in FIG. 3b represent patients who fell below the HBP concentration cut off level but scored above the HBP/WBC ratio cut off level.
Figure 4A:
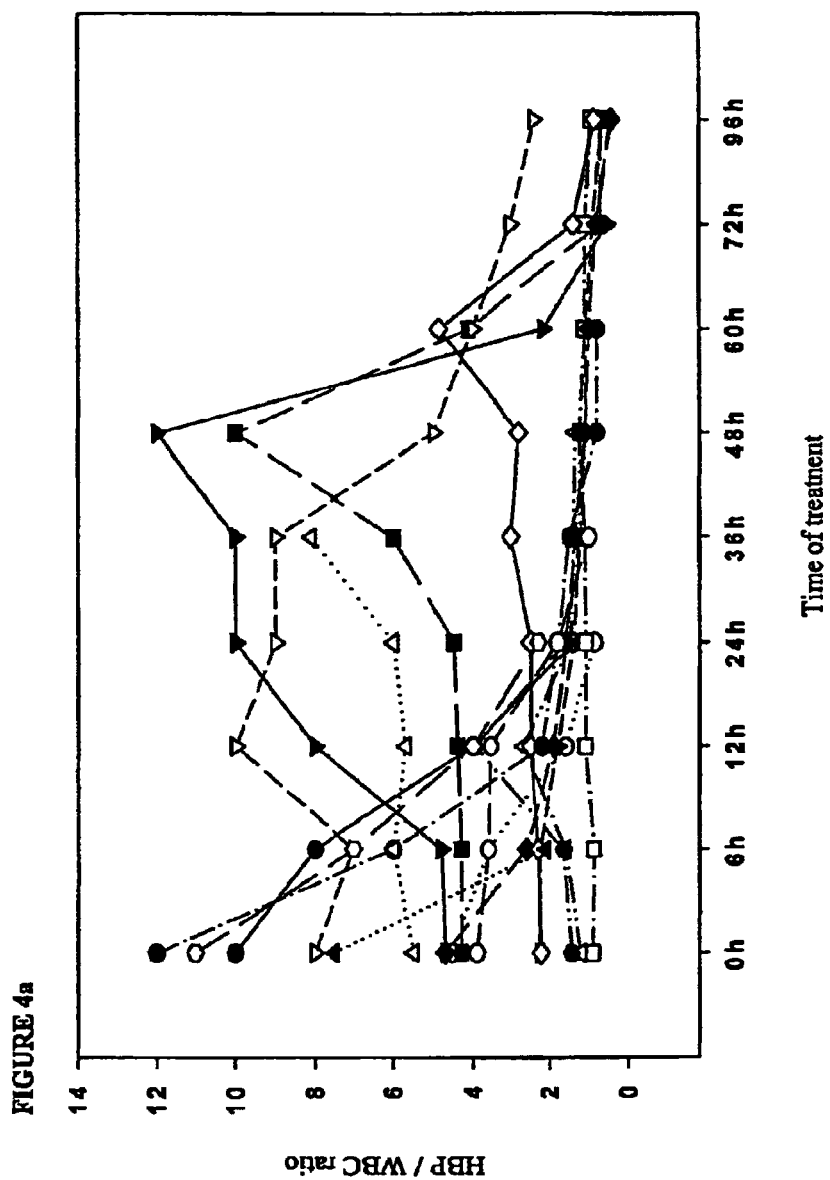
FIG. 4 shows the change in HBP/WBC ratio in consecutive plasma samples taken from 16 patients with severe sepsis over 96 hours (FIGS. 4a) and 7 patients with sepsis, infection without SIRS or no infection over 72 hours (FIG. 4b). Each line represents an individual patient.

HBP Level and HBP/WBC Ratio Predict Severe Sepsis Before Onset of Clinical Symptoms In 20 of the 51 patients in the severe sepsis group the HBP value was elevated up to 12h before the lowest SBP was reached (FIGS. 3a and 3b). The HBP levels rapidly decreased within 24h in the 11 patients who were treated with adequate antibiotics and intravenous fluids and who recovered without complications. In 5 cases where the patients continued to be circulatory unstable the HBP levels, however, remained elevated, 1 of these patient died within 28 days of the inclusion date (FIG. 4a).

Figure 4B:
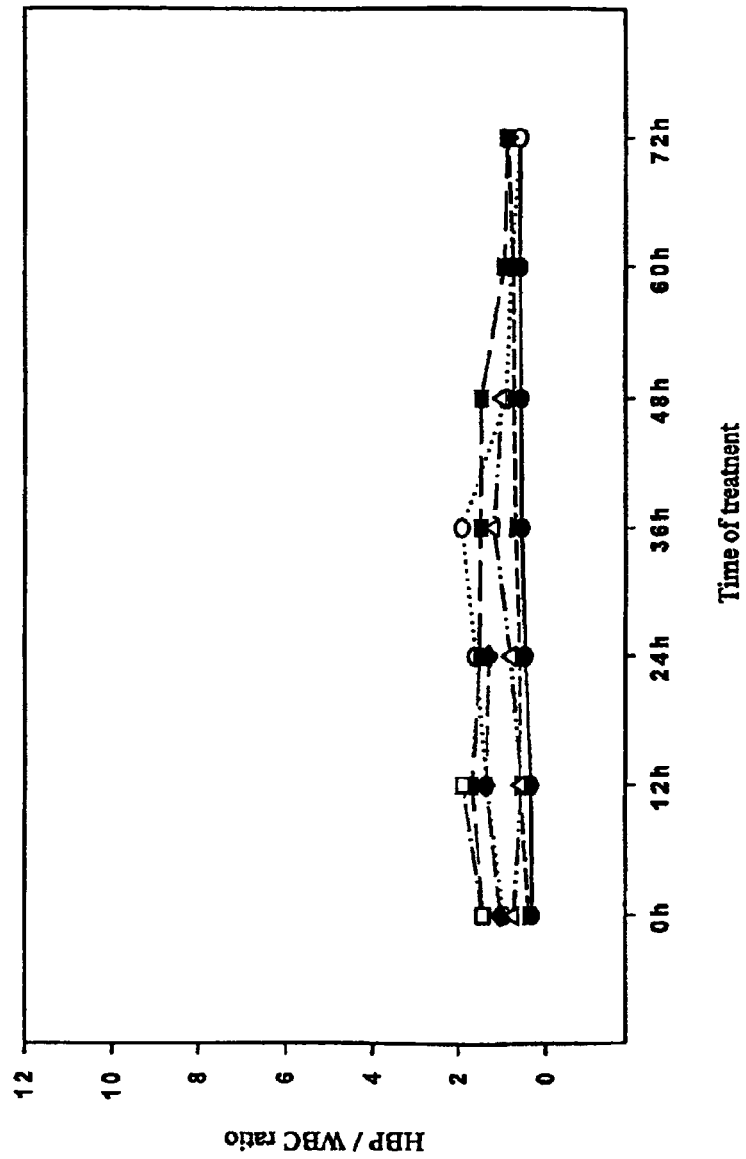

In all 5 patients died, all in the severe sepsis group and all within 1-4 days after the last collected elevated HBP sample. The HBP levels remained low below 20 ng/m1 in 6 patients with sepsis and 1 patient with non-sepsis who were followed with serial sampling (FIG. 4b).

20 patients in the severe sepsis group had increased HBP levels or HBP/WBC ratios at admission but normal SBP, indicating that these indicators are able to predict severe sepsis before standard clinical diagnosis is possible. This is exemplified by a 70-year-old woman presenting with a 3-day history of fever, diarrhoea and vomiting. The physical examination was unremarkable except for fever 38° C., pulse rate 100 but normal SBP of 130 nun/Hg, and she was hospitalized with a tentative diagnosis of gastroenteritis. She was given 1000 ml i.v. crystalloid fluid. Six hours later she developed severe hypotension with SBP 70 mm/Hg, respi- TABLE 1b Sensitivity and specificity of different cut off levels of HBP in diagnosing severe bacterial sepsis

| HBP cut off (ng/ml) | Specificity | Sensitivity |
|---|---|---|
| >15 | 95.1 | 88.2 |
| >16 | 98.0 | 88.2 |
| >17 | 98.6 | 84.3 |
| >19 | 98.6 | 84.3 |
| >20 | 99.3 | 82.4 |
| >21 | 99.3 | 80.4 |
| >22 | 99.3 | 78.4 |
| >23 | 99.3 | 76.5 |
| >24 | 99.3 | 74.5 |

TABLE 1c

Sensitivity and specificity of different cut off levels of HBP/WBC ratio in diagnosing severe bacterial sepsis

| HBP/WBC ratio cut off | Specificity | Sensitivity |
|---|---|---|
| 1.4 | 87.1 | 92.2 |
| 1.5 | 95.0 | 88.2 |
| 1.7 | 95.5 | 86.3 |
| 1.8 | 96.3 | 86.3 |
| 1.9 | 98.0 | 86.3 |
| 2.0 | 98.6 | 86.3 |
| 2.1 | 98.6 | 84.3 |
| 2.2 | 98.6 | 81.4 |
| 2.3 | 98.6 | 78.4 |
| 2.4 | 98.6 | 74.5 |
| 3.6 | 99.3 | 54.9 |

TABLE 2

Analysis of ROC curve for tested variables in diagnosing severe bacterial sepsis

| Test Result Variable (s) | Area Under Curve | Std. Error (a) | Asymptotic Sig. (b) | Asymptotic 95% Confidence Interval | |
|---|---|---|---|---|---|
| | | | | Lower Bound | Upper Bound |
| HBP (ng/ml) | .954 | .017 | .000 | .920 | .988 |
| HBP/WBC ratio | .949 | .022 | .000 | .905 | .993 |
| HBP/WBC ratio or HBP level (ng/ml) | .960 | .019 | .000 | .923 | .997 |
| CRP (mg/ml) | .719 | .040 | .000 | .641 | .797 |
| IL6 (pg/ml) | .789 | .038 | .000 | .714 | .863 |
| Lactate (mmol/l) | .769 | .050 | .000 | .697 | .841 |
| WBC count | .511 | .050 | .820 | .413 | .608 |

The invention claimed is:

1. A method of detecting onset or presence of severe sepsis in an individual, the method comprising:
    providing a blood sample or fraction thereof obtained from an individual suspected of being at risk of developing severe sepsis;
    contacting the sample with an antibody which is capable of binding specifically to Heparin Binding Protein (HBP; Cationic Anti-microbial Protein 37; Azurocidin);
    quantitating the amount of antibody-HBP complex to measure the HBP level in the sample; and
    detecting onset or presence of severe sepsis in the individual at about 88% Sensitivity or lower and about 95% Specificity or greater based on the measured HBP level in the sample.

2. The method according to claim 1, wherein the individual is a mammal.

3. The method according to claim 2, wherein the mammal is a human.

4. The method according to claim 3, wherein the % Sensitivity and % Specificity are based on a Receiver Operating Characteristic (ROC) of HBP levels in blood or fraction thereof for severe sepsis.

5. The method according to claim 3, wherein the detecting of onset or presence of severe sepsis at about 88% Sensitivity or lower and about 95% Specificity or greater has a threshold level of HBP in blood or fraction thereof of about 15 ng/mL or higher.

6. The method according to claim 3, wherein the blood sample or fraction thereof is serum or plasma.

7. The method according to claim 3, wherein the detecting is prior to manifestation of clinical symptoms of severe sepsis.

8. The method according to claim 3, wherein the individual suspected of being at risk for severe sepsis has a confirmed or suspected infection and/or displays one or more of Severe Inflammatory Response (SIRS) criteria.

9. The method according to claim 3, wherein the individual has a confirmed or suspected infection and/or displays two or more of Severe Inflammatory Response (SIRS) criteria.

10. The method according to claim 3, wherein the quantitating of the antibody-HBP complex is by a dipstick assay, wherein the dipstick comprises the antibody which binds specifically to HBP.

11. The method according to claim 3, wherein the quantitating of the antibody-HBP complex is by enzyme linked immunosorbent assay (ELISA).

12. The method according to claim 11, wherein the ELISA is a sandwich ELISA assay.

* * * * *